(12) United States Patent
Nishibayashi et al.

(10) Patent No.: US 6,346,083 B1
(45) Date of Patent: Feb. 12, 2002

(54) BLOOD-PRESSURE MEASURING DEVICE

(75) Inventors: Hideo Nishibayashi, Inuyama; Tomohiro Nunome, Komaki, both of (JP)

(73) Assignee: Colin Corporation, Komaki (JP)

( * ) Notice: Subject to any disclaimer, the term of this patent is extended or adjusted under 35 U.S.C. 154(b) by 23 days.

(21) Appl. No.: 09/613,767

(22) Filed: Jul. 11, 2000

(30) Foreign Application Priority Data

Sep. 6, 1999 (JP) .......................................... 11-251177

(51) Int. Cl.[7] ................................................ A61B 5/02
(52) U.S. Cl. ........................ 600/490; 600/485; 600/494
(58) Field of Search ................................. 600/481, 485, 600/490, 493–496, 500

(56) References Cited

U.S. PATENT DOCUMENTS 5,094,244 A     3/1992  Callahan et al.
5,865,756 A  *  2/1999  Peel, III ................. 600/485 X

FOREIGN PATENT DOCUMENTS

DE          19 40 575 A      3/1971

\* cited by examiner

*Primary Examiner*—Robert L. Nasser
*Assistant Examiner*—Ryan Carter
(74) *Attorney, Agent, or Firm*—Oliff & Berridge, PLC

(57) ABSTRACT

A blood-pressure measuring apparatus including a cuff having an inflatable bag, a first pulse-wave sensor which detects a first pulse wave propagated to the bag, a second pulse-wave sensor which detects a second pulse wave propagated to a downstream-side portion of the cuff wound around a body portion of a subject in a direction of flow of blood in an artery of the body portion, an amplitude correcting device for correcting a first group of respective amplitudes of heartbeat-synchronous pulses of the first pulse wave and/or a second group of respective amplitudes of heartbeat-synchronous pulses of the second pulse wave, so that one or more amplitudes of the first group that correspond to one or more pulses of the first pulse wave that are detected while the flow of blood is stopped by the inflated bag is equal to one or more amplitudes of the second group that correspond to one or more pulses of the second pulse wave that are detected while the flow of blood is stopped by the bag, an amplitude-difference determining device for determining, after the correction, a difference between each of the amplitudes of the first group and a corresponding one of the amplitudes of the second group, and a blood-pressure determining device for determining a blood pressure of the subject based on the respective differences between the respective amplitudes of the first group and the corresponding amplitudes of the second group.

10 Claims, 5 Drawing Sheets

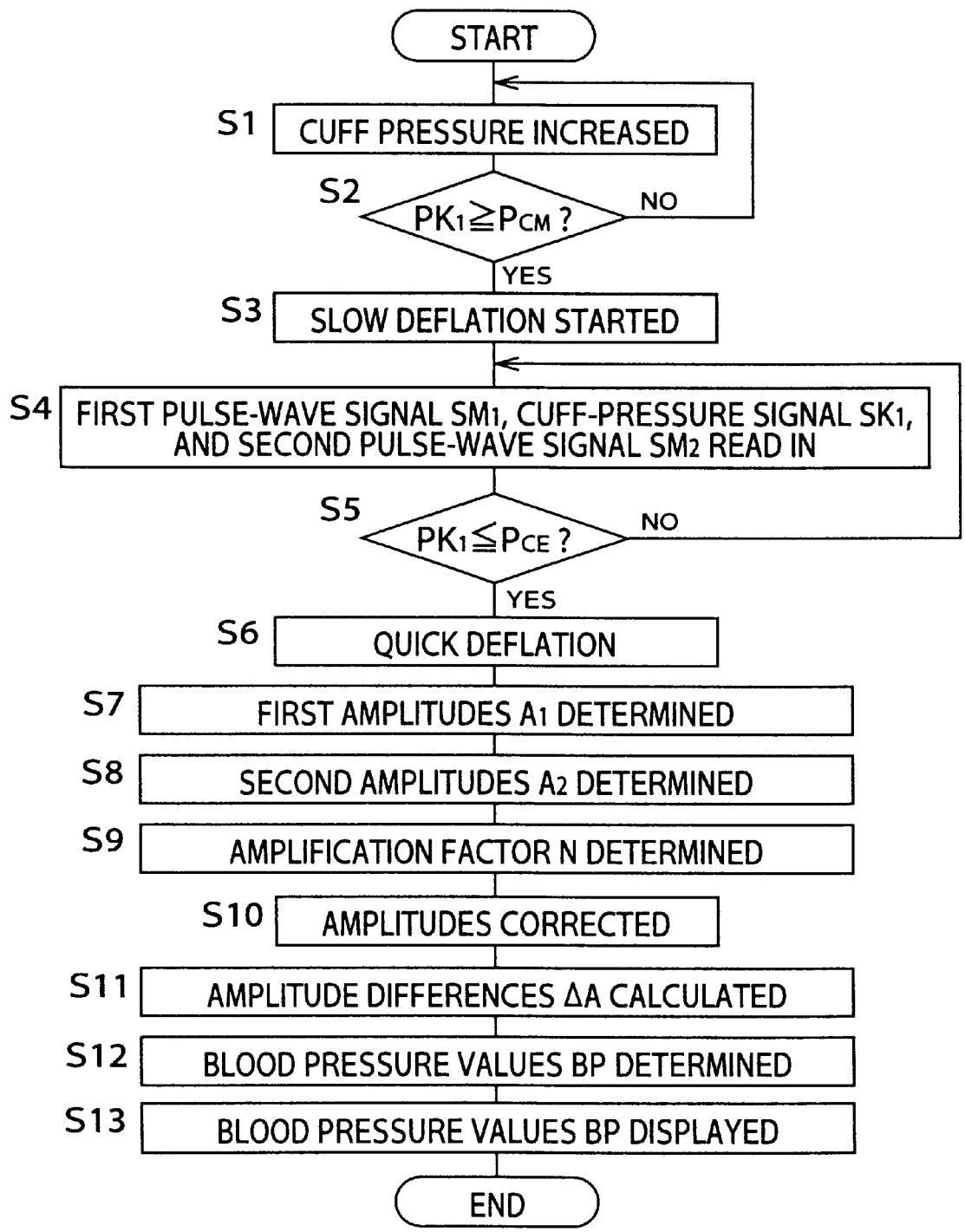

BLOOD-PRESSURE MEASURING DEVICE

BACKGROUND OF THE INVENTION

1. Field of the Invention

The present invention relates to a blood-pressure measuring apparatus which includes an inflatable cuff adapted to be worn on a body portion of a living subject and measures a blood pressure of the subject according to oscillometric method, and particularly to such an apparatus which additionally includes, for improving the accuracy of blood-pressure measurement, a pulse-wave detecting device for detecting a pulse wave propagated to a downstream-side portion of the cuff as seen in a direction of flow of blood in an artery of the body portion and determines a blood pressure of the subject based on the pulse wave detected by the pulse-wave detecting device.

2. Related Art Statement

Generally, an oscillometric-type blood-pressure ("BP") measuring apparatus increases a pressing pressure of an inflatable bag accommodated in a cuff adapted to be wound around a body portion of a living subject, up to a predetermined pressure at which the bag can completely stop the flow of blood in an artery of the body portion under the cuff, subsequently slowly decreases the pressing pressure of the bag while continuously detecting the pressure in the bag, extracts a pulse wave from the continuously detected pressure of the bag, specifies a pressure of the bag at a rising point where respective amplitudes of respective heartbeat-synchronous pulses of the extracted pulse wave significantly largely changes, and determines the specified pressure of the bag as a systolic BP value of the subject.

However, the above BP measuring apparatus may not measure an accurate systolic BP value because the apparatus may not specify an accurate rising point of the pulse amplitudes of the pulse wave. More specifically described, even if the pressing pressure of the cuff may be higher than the systolic BP value of the subject, the pulsation of the artery may be transmitted to an upstream-side portion of the cuff as seen in the direction of flow of blood in the artery. In particular, in the case where the cuff is worn on a certain body portion (e.g., an ankle) of the subject where it is difficult for the cuff to completely stop the blood flow in the artery, a considerably great pulse wave may be transmitted to the upstream-side portion of the cuff while the pressing pressure of the cuff is higher than the systolic BP value of the subject. Accordingly, the pulse amplitudes of the pulse wave show an unclear rising point.

To solve the above problem, it has been proposed to provide a pulse-wave detecting device inside a downstream-side portion of an inflatable bag of a cuff and determine a BP value based on pulse amplitudes detected by the pulse-wave detecting device. For example, the pulse-wave detecting device may be one which includes a pulse-wave-detecting inflatable bag which is independent of the artery-pressing inflatable bag and is provided inside the downstream-side portion of the artery-pressing bag, and a pressure sensor which detects the pressure in the pulse-wave-detecting bag. In this case, a BP value is determined based on pulse amplitudes of a pulse wave transmitted to the pulse-wave-detecting bag. While the pressing pressure of the artery-pressing bag is higher than the systolic BP value of the subject, the pulsation of the artery may be propagated to the artery-pressing bag, but is not directly propagated to the pulse-wave-detecting bag provided inside the downstream-side portion of the artery-detecting bag. Thus, the pulse amplitudes of the pulse wave detected by the pulse-wave detecting device show a clearer rising point, which leads to determining a more accurate BP value.

However, in some cases, even pulse amplitudes of a pulse wave detected by the pulse-wave detecting device do not show a clear rising point. In particular, in the case where the cuff is worn on, e.g., an ankle where it is difficult for the cuff to completely stop the blood flow in the artery, the pulse amplitudes of a pulse wave detected by the pulse-wave detecting device may not show a clear rising point. In this case, while the pressing pressure of the artery-pressing bag is higher than the systolic BP value of the subject, the pulsation of the artery is, indeed, not directly propagated to the pulse-wave-detecting bag provided inside the downstream-side portion of the artery-detecting bag. However, the pulsation may be indirectly propagated to the pulse-wave-detecting bag via the artery-pressing bag. That is, even if the pressing pressure of the artery-pressing bag may be higher than the systolic BP value of the subject, a pulse wave is produced from an artery located on an upstream side of the cuff, and this pulse wave is propagated to an upstream-side portion of the artery-pressing bag of the cuff, and this pulse wave is detected by the pulse-wave sensor via the pulse-wave-detecting bag. Therefore, a BP value determined based on pulse amplitudes of a pulse wave detected by the pulse-wave detecting device may not be accurate.

SUMMARY OF THE INVENTION

It is therefore an object of the present invention to provide a blood-pressure measuring apparatus which measures an accurate blood pressure.

The Applicants have carried out their extensive studies to achieve the above object, and found that it is possible to measure an accurate blood pressure by subtracting, from respective amplitudes of heartbeat-synchronous pulses of a pulse wave detected by a pulse-wave sensor, the influence of respective amplitudes of heartbeat-synchronous pulses of a pulse wave propagated to an inflatable bag employed for pressing an arterial vessel of a living subject, and thereby clearly showing a rising point of the former pulse amplitudes. The present invention has been developed based on this finding.

(1) According to a first feature of the present invention, there is provided a blood-pressure measuring apparatus comprising an inflatable cuff which is adapted to be wound around a body portion of a living subject and which includes a first inflatable bag which is inflatable to press an arterial vessel of the body portion and stop flow of blood in the arterial vessel; a first pulse-wave detecting device which detects a first pulse wave which is produced from the arterial vessel and is propagated to the first inflatable bag of the cuff wound around the body portion, the first pulse wave including a plurality of heartbeat-synchronous pulses; a second pulse-wave detecting device which detects a second pulse wave which is produced from the arterial vessel and is propagated to a downstream-side portion of the cuff wound around the body portion as seen in a direction in which the blood flows in the arterial vessel, the second pulse wave including a plurality of heartbeat-synchronous pulses; amplitude correcting means for correcting at least one of (a) a first group of respective amplitudes of the heartbeat-synchronous pulses of the first pulse wave detected by the first pulse-wave detecting device and (b) a second group of respective amplitudes of the heartbeat-synchronous pulses of the second pulse wave detected by the second pulse-wave detecting device, so that at least one amplitude of the first group that corresponds to at least one heartbeat-synchronous pulse of the first pulse wave that is detected by the first pulse-wave detecting device while the flow of the blood in the arterial vessel is stopped by the first inflatable bag is substantially equal to at least one amplitude of the second group that corresponds to at least one heartbeat-synchronous pulse of the second pulse wave that is detected by the second pulse-wave detecting device while the flow of the blood in the arterial vessel is stopped by the first inflatable bag; amplitude-difference determining means for determining a difference between each of the amplitudes of the first group and a corresponding one of the amplitudes of the second group after the at least one of the first and second groups is corrected by the amplitude correcting means; and blood-pressure determining means for determining a blood pressure of the subject based on the difference between the each of the amplitudes of the first group and the corresponding one of the amplitudes of the second group.

According to this feature, the amplitude correcting means corrects at least one of the first group of amplitudes provided by the first pulse-wave detecting device and the second group of amplitudes provided by the second pulse-wave detecting device, so that one or more amplitudes of the first group that correspond to one or more pulses of the first pulse wave that are detected while the flow of blood in the arterial vessel is stopped by the first inflatable bag is substantially equal to one or more amplitudes of the second group that correspond to one or more pulses of the second pulse wave that are detected while the flow of blood is stopped by the first inflatable bag, and the amplitude-difference determining means determines a difference between each of the amplitudes of the first group and a corresponding one of the amplitudes of the second group after the first and/or second groups is corrected by the amplitude correcting means. The thus obtained amplitude differences show a clear rising point, and the blood-pressure determining means can determine an accurate blood pressure value of the subject based on the change of the respective differences between the respective amplitudes of the first group and the corresponding amplitudes of the second group.

(2) According to a second feature of the present invention that includes the first feature (1), the second pulse-wave detecting device comprises a second inflatable bag which is supported by the inflatable cuff such that the second inflatable bag is located inside a downstream-side portion of the first inflatable bag as seen in the direction in which the blood flows in the arterial vessel, and which has a dimension as measured in the direction that is smaller than a dimension of the first inflatable bag as measured in the direction; and a pressure sensor which detects the second pulse wave produced from the arterial vessel and propagated to the second inflatable bag, and which produces an electric signal representing the detected second pulse wave including the heartbeat-synchronous pulses having the respective amplitudes. According to this feature, the BP measuring device can enjoy a simple construction and accordingly can be produced with ease and at low cost.

(3) According to a third feature of the present invention that includes the second feature (2), the blood-pressure measuring apparatus further comprises a preventing member which prevents the first pulse wave from being transmitted from the first inflatable bag to the second inflatable bag.

(4) According to a fourth feature of the present invention that includes the second or third feature (2) or (3), the first pulse-wave detecting device comprises a pressure sensor which detects the first pulse wave produced from the arterial vessel and propagated to the first inflatable bag, and which produces an electric signal representing the detected first pulse wave including the heartbeat-synchronous pulses having the respective amplitudes.

(5) According to a fifth feature of the present invention that includes the fourth feature (4), the blood-pressure determining means comprises means for determining, as a systolic blood pressure of the subject, a pressure in the first inflatable bag that is detected by the pressure sensor of the first pulse-wave detecting device, at a time when the respective differences between the amplitudes of the first group and the corresponding amplitudes of the second group significantly change as the pressure of the first inflatable bag changes.

(6) According to a sixth feature of the present invention that includes any one of the first to fifth features (1) to (5), the blood-pressure measuring apparatus further comprises a pressure changing device which changes a pressure in the first inflatable bag of the cuff wound around the body portion to press the arterial vessel and stop the flow of the blood in the arterial vessel.

(7) According to a seventh feature of the present invention that includes any one of the first to sixth features (1) to (6), the blood-pressure measuring apparatus further comprises first amplitude determining means for determining the respective amplitudes of the heartbeat-synchronous pulses of the first pulse wave that are detected by the first pulse-wave detecting device while the pressure of the first inflatable bag is changed by the pressure changing device, and thereby providing the first group of amplitudes; and second amplitude determining means for determining the respective amplitudes of the heartbeat-synchronous pulses of the second pulse wave that are detected by the second pulse-wave detecting device while the pressure of the first inflatable bag is changed by the pressure changing device, and thereby providing the second group of amplitudes.

(8) According to an eighth feature of the present invention that includes any one of the first to seventh features (1) to (7), the amplitude correcting means comprises amplification-factor determining means for determining an amplification factor based on at least one amplitude of the first group that corresponds to the at least one heartbeat-synchronous pulse of the first pulse wave that is detected by the first pulse-wave detecting device while the flow of the blood in the arterial vessel is stopped by the first inflatable bag, and at least one amplitude of the second group that corresponds to the at least one heartbeat-synchronous pulse of the second pulse wave that is detected by the second pulse-wave detecting device while the flow of the blood in the arterial vessel is stopped by the first inflatable bag; and calculating means for calculating a product of the amplification factor and each of the amplitudes of the at least one of the first and second groups, and thereby correcting the at least one of the first and second groups.

(9) According to a ninth feature of the present invention that includes any one of the first to eighth features (1) to (8), the amplification-factor determining means comprises means for determining the amplification factor by dividing an average of a plurality of amplitudes of the first group that corresponds to a plurality of heartbeat-synchronous pulse of the first pulse wave that are detected by the first pulse-wave detecting device while the flow of the blood in the arterial vessel is stopped by the first inflatable bag, by an average of a plurality of amplitudes of the second group that corresponds to a plurality of heartbeat-synchronous pulse of the second pulse wave that are detected by the second pulse-wave detecting device while the flow of the blood in the arterial vessel is stopped by the first inflatable bag, and wherein the calculating means calculates a product of the amplification factor and each of the amplitudes of the second groups, and thereby correcting the second groups, and the amplitude-difference determining means determines a difference between each of the amplitudes of the first group and a corresponding one of the amplitudes of the second group that have been corrected by the amplitude correcting means.

(10) According to a tenth feature of the present invention that includes any one of the first to ninth features (1) to (9), the blood-pressure measuring apparatus further comprises a display device which displays the blood pressure of the subject determined by the blood-pressure determining means.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 5 is a flow chart representing a control program according to which the control device of the apparatus of FIG. 1 is operated to measure a BP value of the subject.

DETAILED DESCRIPTION OF THE PREFERRED EMBODIMENTS

Hereinafter, there will be described a blood-pressure ("BP") measuring apparatus 10 embodying the present invention, by reference to the drawings.

Figure 1:
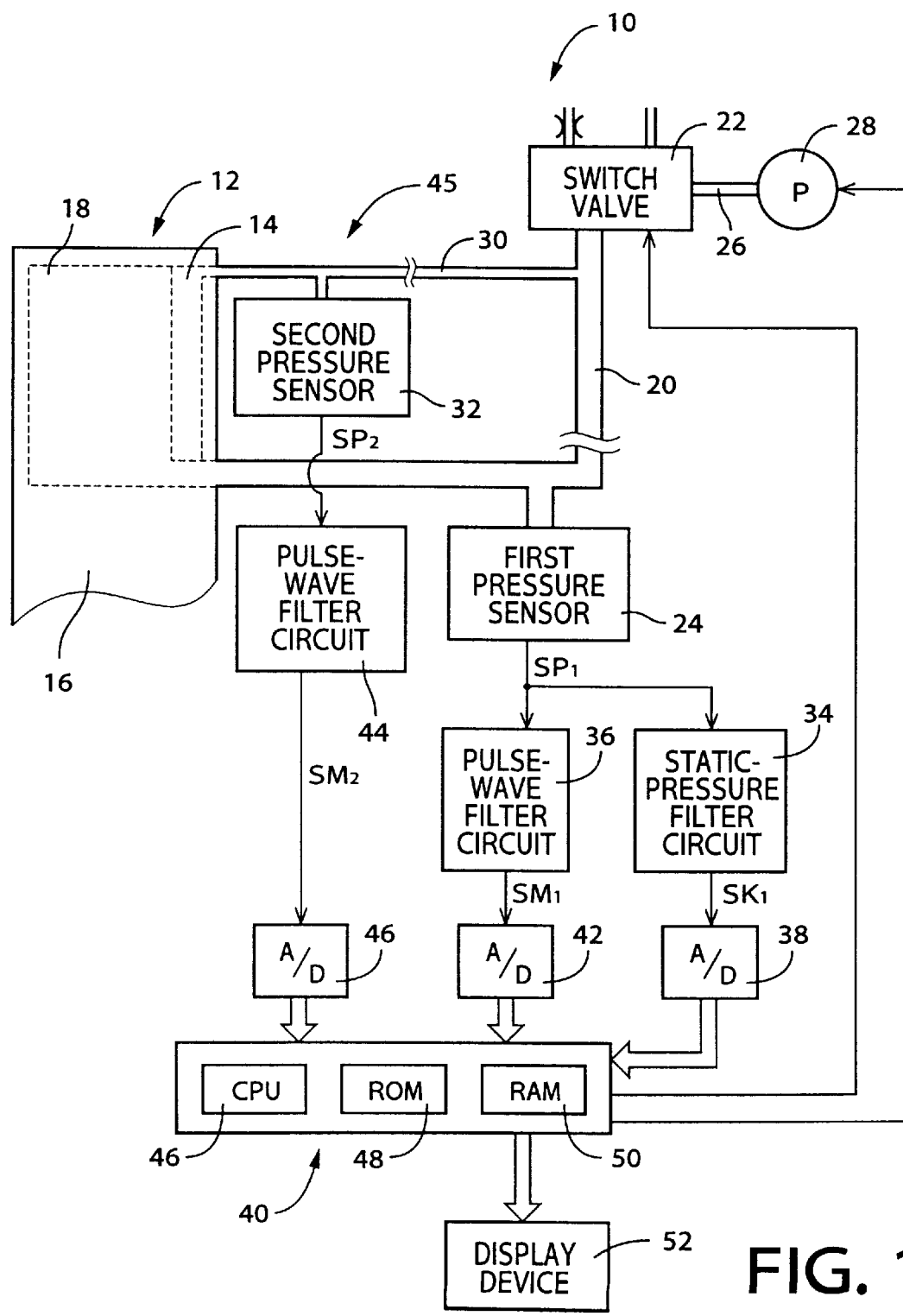
FIG. 1 is a diagrammatic view for explaining the construction of a blood-pressure ("BP") measuring apparatus to which the present invention is applied.

In FIG. 1, reference numeral 12 designates an inflatable cuff which is for being wound around an ankle 19 (FIG. 2) of a living subject and which differs from a conventional inflatable cuff used for being wound around an ankle in that the present cuff 12 additionally includes a second rubber bag 14 as a second inflatable bag, described below. More specifically described, the cuff 12 includes a belt-like cloth bag which is formed of a non-extensible and considerably hard cloth and has a shape suitable for being wound around an ankle of a human being; and a first rubber bag 18 which is accommodated in the cloth bag and which has a width slightly shorter than that of the cloth bag 16 and a predetermined length shorter than than the circumferential length of the ankle 19 (e.g., length equal to two thirds of an average circumferential length of an ankle). The first rubber bag 18 provides a first inflatable bag which is used mainly for pressing arteries 21 of the ankle 19 and stopping the flow of blood in the arteries 21.

Figure 2:
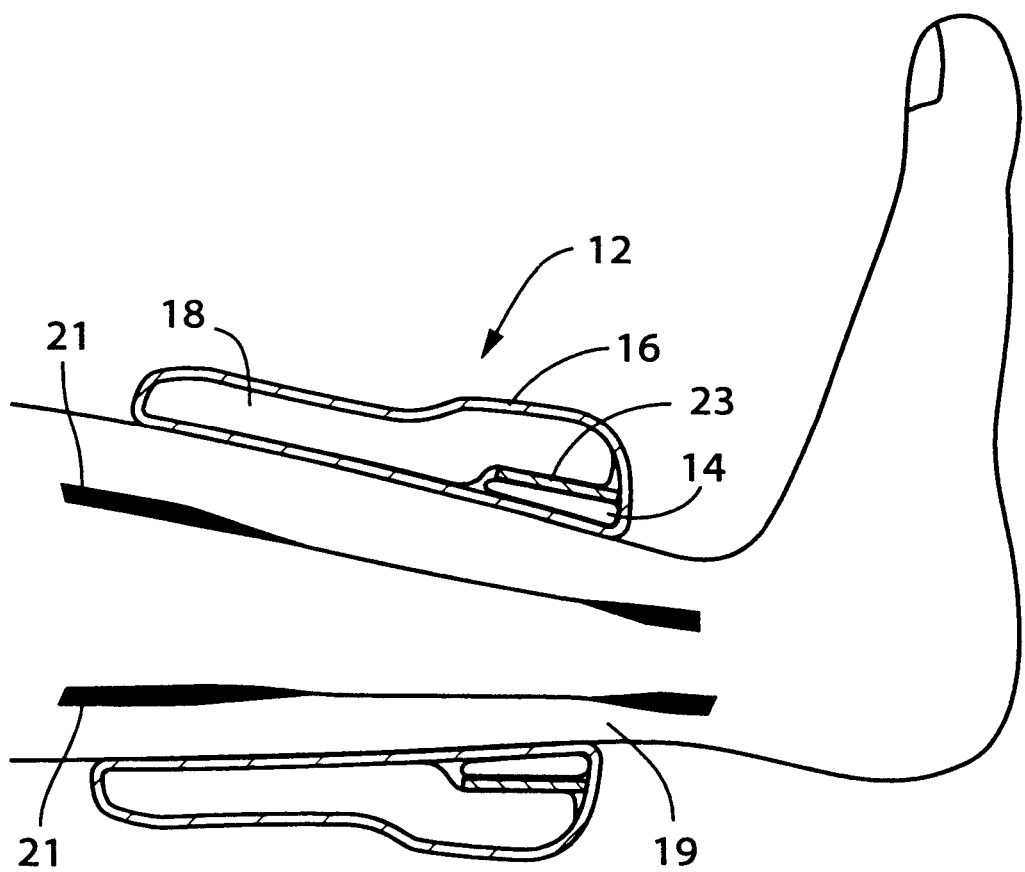
FIG. 2 is a view for explaining a state in which an inflatable cuff of the apparatus of FIG. 1 is wound around an ankle of a living subject and occludes arterial vessels of the ankle.

In addition, the cloth bag 16 accommodates, as shown in FIG. 2, a second rubber bag 14 at a location inside a downstream-side end portion of the first rubber bag 18 as seen in the direction in which the blood flows in the arteries 21, in the state in which the cuff 12 is worn on the ankle 19. The second rubber bag 14 has a length substantially equal to the length of the first rubber bag 18, and a width equal to from one fourth to one sixth of the width of the first bag 18. The second rubber bag 18 is used mainly for detecting pulsation of the arteries 21 of the ankle 19. FIG. 2 shows the state in which the cuff 12 constructed as described above is wound around the ankle 19 of the subject and occludes the arteries 21 of the ankle 19. As shown in FIG. 2, a shield plate 23 as a preventing member is provided between the first and second rubber bags 18, 14. The shield plate 23 is for preventing the oscillation produced in the first bag 18 from being transmitted to the second bag 14. The shield plate 23 has substantially the same width and length as those of the second rubber bag 14, has a thickness of about 0.3 mm, and is formed of a considerably hard, flexible material. The shield plate 23 is omitted from the cuff 12 shown in FIG. 1.

The first rubber bag 18 is connected to a switch valve 22 and a first pressure sensor 24 via a pipe 20, and the switch valve 22 is connected to an air pump 28 via a pipe 26. The second rubber bag 14 is connected to the switch valve 22 and a second pressure sensor 32 via a pip 30 branched from the pipe 20 connected to the first rubber bag 18. Since the pipe 30 connected to the second rubber bag 14 has a diameter smaller than that of the pipe 20 connected to the first rubber bag 18, the pipe 30 functions as an air-restricting device.

The switch valve 22 is switchable to each of three operation states, i.e., a pressure-supply state in which the switch valve 22 allows a pressurized air to be supplied from the air pump 28 to the cuff 12, i.e., the first and second rubber bags 18, 14, a slow-deflation state in which the switch valve 22 allows the pressurized air to be slowly deflated from the cuff 12, and a quick-deflation state in which the switch valve 22 allows the pressurized air to be quickly deflated from the cuff 12.

The first pressure sensor 24 detects an air pressure, $P_1$, in the first rubber bag 18, produces a first pressure signal, $SP_1$, representing the detected air pressure $P_1$, and supplies the first pressure signal $SP_1$, to a static-pressure filter circuit 34 and a pulse-wave filter circuit 36. The static-pressure filter circuit 34 includes a low-pass filter which extracts, from the first pressure signal $SP_1$, a constant component representing a static pressure of the first rubber bag 18, produces a cuff-pressure signal, $SK_1$, representing the static pressure, i.e., the cuff pressure, $PK_1$, and supplies the cuff-pressure signal $SK_1$ to a control device 40 via an analog-to-digital ("A/D") converter 38. The pulse-wave filter circuit 36 includes a band-pass filter which extracts, from the first pressure signal $SP_1$, an oscillatory component representing a first pulse wave transmitted to the first rubber bag 18, produces a first pulse-wave signal, $SM_1$, representing the first pulse wave, and supplies the first pulse-wave signal $SM_1$ to the control device 40 via an A/D converter 42. The first pulse wave represented by the first pulse-wave signal $SM_1$ is an oscillatory pressure wave which is produced from the arteries 21 of the ankle 19 under the cuff 12 in synchronism with the heartbeat of the subject and is propagated from the arteries 21 to the first rubber bag 18. Thus, the first rubber bag 18, the first pressure sensor 24, and the first pulse-wave filter circuit 34 cooperate with one another to provide a first pulse-wave detecting device. The first pulse wave represented by the first pulse-wave signal $SM_1$ consists of successive heartbeat-synchronous pulses which are successively produced from the arteries 21 in synchronism with successive beats of the heart of the subject.

The second pressure 32 detects an air pressure, $P_2$, in the second rubber bag 14, produces a second pressure signal, $SP_2$, representing the detected air pressure $P_2$, and supplies the second pressure signal $SP_2$ to a pulse-wave filter circuit 44. The pulse-wave filter circuit 44 has the same construction as that of the above-described pulse-wave filter circuit 36 connected to the first pressure sensor 24, i.e., includes a band-pass filter which extracts, from the second pressure signal $SP_2$, an oscillatory component representing a second pulse wave transmitted to the second rubber bag 14, produces a second pulse-wave signal, $SM_2$, representing the second pulse wave, and supplies the second pulse-wave signal $SM_2$ to the control device 40 via an A/D converter 46. The second pulse wave represented by the second pulse-wave signal $SM_2$ is an oscillatory pressure wave which is produced from the arteries 21 of the ankle 19 under the cuff 12 in synchronism with the heartbeat of the subject and is propagated from the arteries 21 to the second rubber bag 14. Thus, the second rubber bag 14, the second pressure sensor 32, and the second pulse-wave filter circuit 44 provides a second pulse-wave detecting device 45. The second pulse wave represented by the second pulse-wave signal $SM_2$ consists of successive heartbeat-synchronous pulses which are successively produced from the arteries 21 in synchronism with successive beats of the heart of the subject, like the first pulse wave represented by the first pulse-wave signal $SM_1$.

The control device 40 is constituted by a so-called microcomputer including a central processing unit ("CPU") 46, a read only memory ("ROM") 48, a random access memory ("RAM") 50, and an input-and-output ("I/O") port (not shown). The CPU 46 processes signals according to control programs pre-stored in the ROM 48, by utilizing a temporary-storage function of the RAM 50, and outputs, via the I/O port, drive signals to respective drive circuits (not shown) of the switch valve 22 and the air pump 28. While the switch valve 22 and the air pump 28 are thus controlled, the CPU 46 obtains the first pressure signal $SP_1$ supplied from the static-pressure filter circuit 34, and the first and second pulse-wave signals $SM_1$, $SM_2$ supplied from the pulse-wave-filter circuits 36, 46, determines a BP value BP of the subject based on the thus obtained signals $SP_1$, $SM_1$, $SM_2$, and operates a display device 52 to display the thus determined BP value BP.

Figure 3:
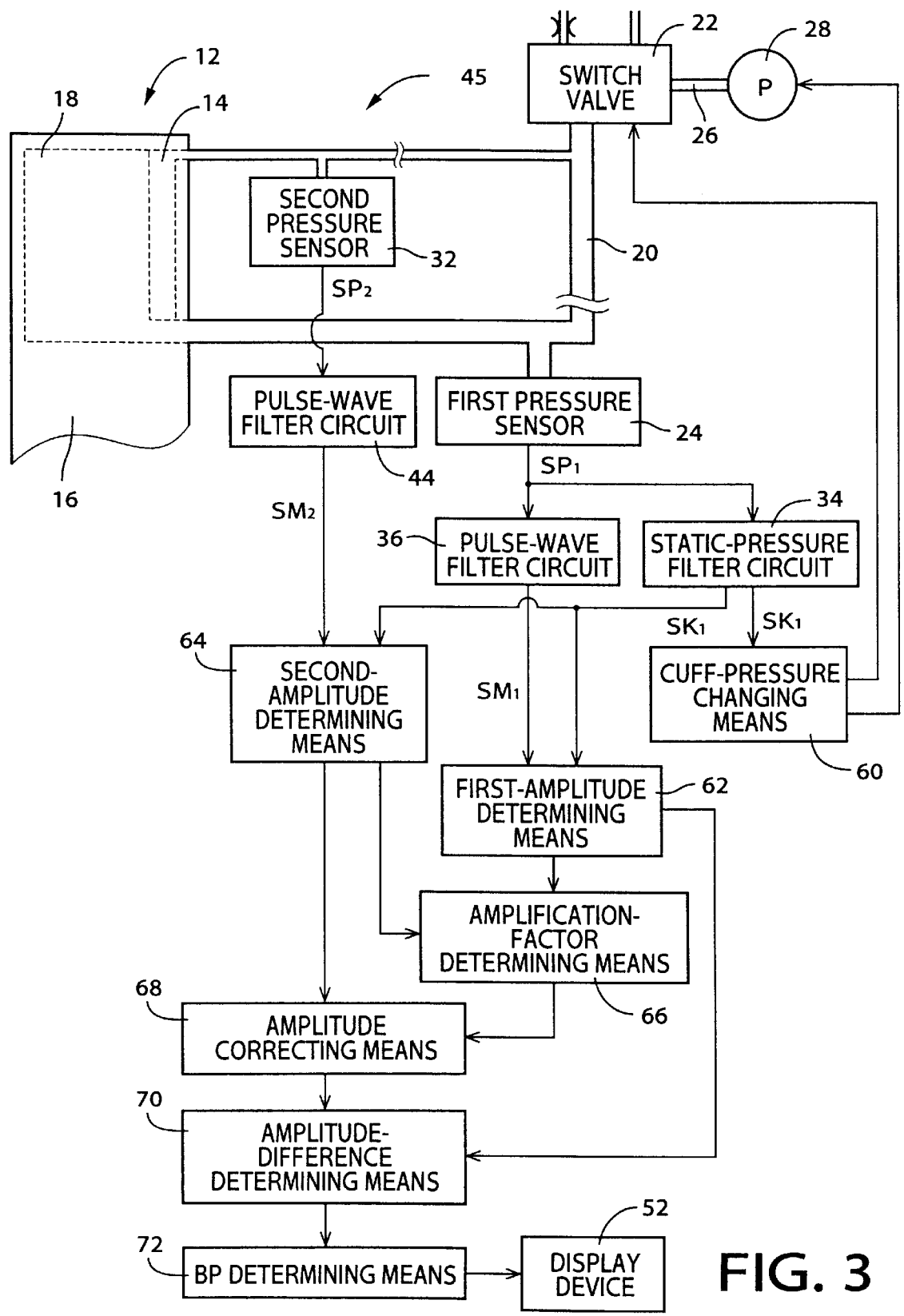
FIG. 3 is a diagrammatic view for explaining essential control functions of a control device of the apparatus of FIG. 1.

FIG. 3 shows essential control functions of the control device 40 of the BP measuring apparatus 10 constructed as described above. A cuff-pressure changing means 60 starts the air pump 28, and switches the switch valve 22 to its pressure-supply state, to quickly increase the pressure in the cuff 12 wound around the ankle 19 of the subject. When the first cuff-pressure signal $P_1$ in the first rubber bag 18 that is detected by the first pressure sensor 24 reaches a predetermined target pressure value, $P_{CM}$, (e.g., 230 mmHg), the changing means 60 switches the switch valve 22 to its slow-deflation state to slowly decrease the pressure of the cuff 12 at a predetermined low rate of, e.g., 3 mmHg/sec. When the pressing pressure of the cuff 12 is lowered down to a predetermined measurement-end pressure value, $P_{CE}$, which is sufficiently lower than a diastolic BP value, $BP_{DIA}$, of the patient, the changing means 60 switches the switch valve 22 to its quick-deflation state, and stops the air pump 28.

Figure 4:
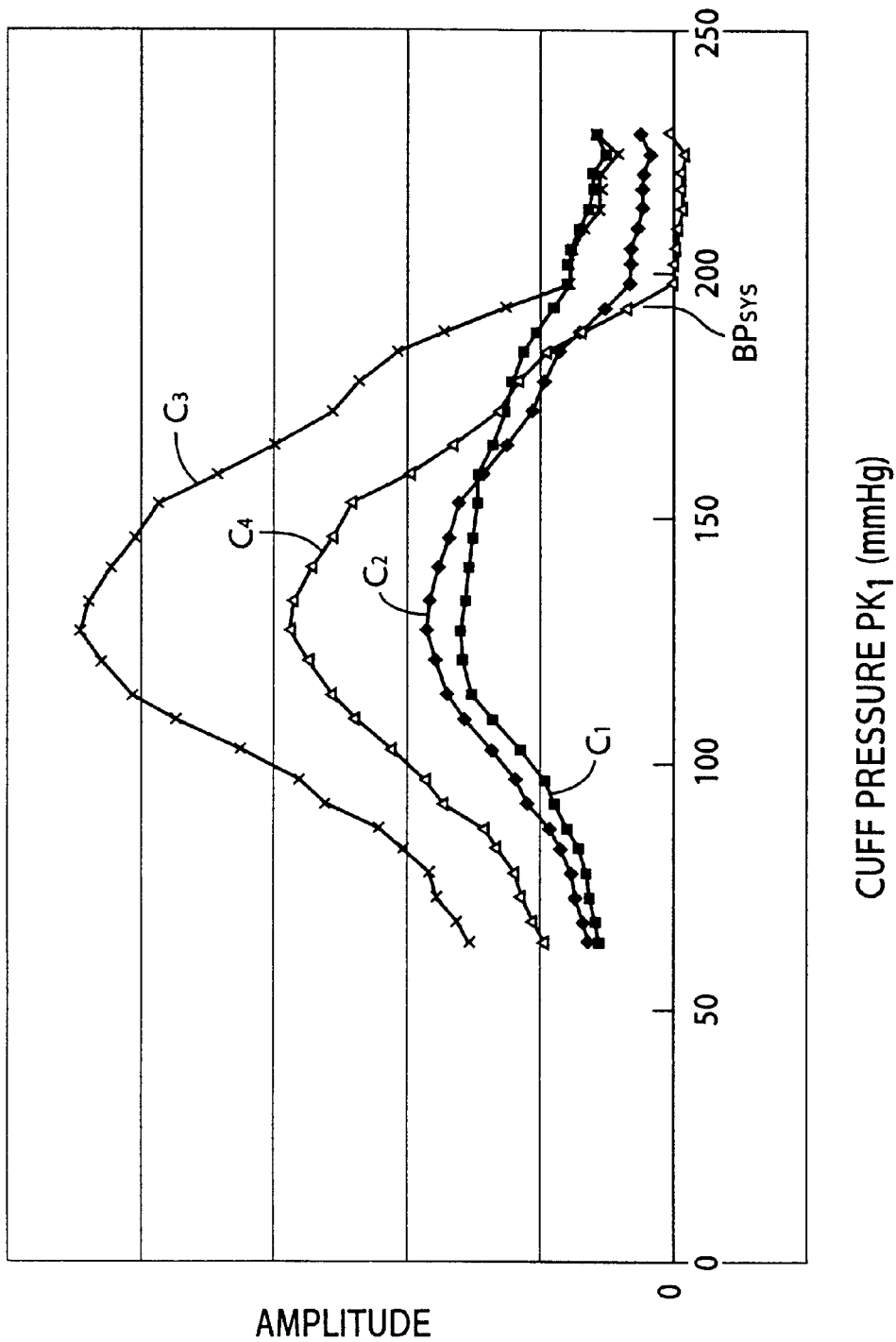
FIG. 4 is a graph showing a curve, $C_1$, representing change of first amplitudes $A_1$, a curve, $C_2$, representing change of second amplitudes $A_2$, a curve, $C_3$, representing change of corrected amplitudes $A_{2-1}$ obtained by multiplying the second amplitudes $A_2$ by an amplification factor, N, and a curve, $C_4$, representing change of amplitude differences $\Delta A$ obtained by subtracting the first amplitudes $A_1$ from the corresponding corrected amplitudes $A_{2-1}$.

A first-amplitude determining means 62 reads, when the pressing pressure of the cuff 12 is slowly lowered by the cuff-pressure changing means 60, the first pulse-wave signal $SM_1$ which is extracted by the first pulse-wave filter circuit 36 as the oscillatory component of the first pressure $P_1$ detected by the first pressure sensor 24, determines an amplitude (hereinafter, referred to as the "first amplitude, $A_1$") of each of successive heartbeat-synchronous pulses of the read first pulse-wave signal $SM_1$, and stores the determined first amplitude $A_1$ with a cuff pressure $PK_1$ detected when the each pulse is detected, in a predetermined first-amplitude memory area of the RAM 50. A curve, $C_1$, shown in FIG. 4 represents the change of respective first amplitudes $A_1$ of the successive heartbeat-synchronous pulses of the first pulse-wave signal $SM_1$, with respect to the change of the cuff pressure $PK_1$. While the cuff pressure $PK_1$ is higher than a systolic BP value, $BP_{SYS}$, which is determined by a BP determining means 72, described later, the flow of blood in the arteries 21 under the cuff 12 is stopped by the pressing of the cuff 12. Thus, the arteries 21 do not pulsate under the second rubber bag 14 located in the downstream-side portion of the cuff 12 wound around the ankle 19. However, even if the cuff pressure $PK_1$ is changed in a range higher than the systolic BP value $BP_{SYS}$, the arteries 21 pulsate under the upstream-side portion of the first rubber bag 18, such that as the cuff pressure $PK_1$ decreases, the pulsation of the arteries 21 increases. Since this pulsation is propagated to the first rubber bag 18, the curve $C_1$ indicates considerably great amplitudes $A_1$ already at the beginning of the slow deflation of the cuff 12 from the target pressure value $P_{CM}$, and does not show a clear rising point where the first amplitudes $A_1$ significantly increase as the cuff pressure $PK_1$ decreases from the target pressure value $P_{CM}$.

A second-amplitude determining means 64 reads, when the pressing pressure of the cuff 12 is slowly lowered by the cuff-pressure changing means 60, the second pulse-wave signal $SM_2$ which is extracted by the second pulse-wave filter circuit 44 as the oscillatory component of the second pressure $P_2$ detected by the second pressure sensor 24, determines an amplitude (hereinafter, referred to as the "second amplitude, $A_2$") of each of successive heartbeat-synchronous pulses of the read second pulse-wave signal $SM_2$, and stores the determined second amplitude $A_1$ with a cuff pressure $PK_1$ detected when the each pulse is detected, in a predetermined second-amplitude memory area of the RAM 50. A curve, $C_2$, shown in FIG. 4 represents the change of respective second amplitudes $A_2$ of the successive heartbeat-synchronous pulses of the second pulse-wave signal $SM_2$, with respect to the change of the cuff pressure $PK_1$. At the beginning of the slow deflation of the cuff 12, the second amplitudes $A_2$ of the curve $C_2$ are smaller than the first amplitudes $A_1$ of the curve $C_1$, and have a clearer rising point than that of the first amplitudes $A_1$, as shown in FIG. 4. However, even the rising point of the curve $C_2$ is not sufficiently clear. This is caused by the fact that the second rubber bag 14 is protected to some degree by the shield plate 23 against the oscillation of the pressure in the first rubber bag 18, but is not completely protected, so that the second rubber bag 14 is influenced by the pressure oscillation of the first rubber bag 18. In addition, the pressure oscillation of the first rubber bag 18 is transmitted to the second rubber bag 14 via a route provided by the pipe 20 and the pipe 30.

An amplification-factor determining means 66 determines an amplification factor, N, (N is equal, or greater than, one) which is to be used to amplify the second pressure $P_2$ detected by the second pressure sensor 32, so that one or more first amplitudes $A_1$ determined by the first-amplitude determining means 62 from one or more heartbeat-synchronous pulses of the first pulse-wave signal $SM_1$ detected in a blood-stop pressure range in which the flow of blood in the arteries 21 is stopped by the cuff 12 (i.e., the first rubber bag 18) are substantially equal to one or more second amplitudes $A_2$ which are determined by the second-amplitude determining means 64 from one or more heartbeat-synchronous pulses of the second pulse-wave signal $SM_2$ detected in the blood-stop pressure range and then are amplified with the determined amplification factor N. The blood-stop pressure range is a range of the cuff pressure $PK_1$ between the target pressure $P_{CM}$, and a reference pressure, $P_B$, not lower than the systolic BP value $BP_{SYS}$ of the subject. The reference pressure $P_B$ may be a constant value which is determined in advance based on respective systolic BP values of many patients and accordingly is usable for many individual persons; a value which is determined in advance based on, e.g., the age of the subject; a value which is input in advance through an input device (not shown); or a value at which the rate of change of the second amplitudes $A_2$ determined by the means 64 exceeds a predetermined value.

An amplitude correcting means 68 corrects each of the second amplitudes $A_2$ determined by the means 64, by calculating the product of the each second amplitude $A_2$ and the amplification factor N determined by the means 66. The thus corrected second amplitudes will be referred to as the corrected amplitudes $A_{2-1}$. A curve, $C_3$, shown in FIG. 4 represents the change of the corrected amplitudes $A_{2-1}$ with respect to the change of the cuff pressure $PK_1$.

An amplitude-difference determining means 70 determines a difference $\Delta A$ between each of the corrected amplitudes $A_{2-1}$ and a corresponding one of the first amplitudes $A_1$, by subtracting, from the each corrected amplitude $A_{2-1}$, the corresponding one first amplitude $A_1$. A curve, $C_4$, shown in FIG. 4 represents the change of the thus determined amplitude differences $\Delta A$. Since the curve $C_4$ is obtained by removing the influence of the first amplitudes $A_1$ occurring to the first rubber bag 18, from the second amplitudes $A_2$ detected by the second pulse-wave detecting device 45, the curve $C_4$ is substantially equal to zero in the blood-stop pressure range of the cuff pressure $PK_1$, and shows a clear rising point.

A BP determining means 72 determines, according to oscillometric method, one or more BP values of the subject based on the change of the amplitude differences $\Delta A$. More specifically described, first, the means 72 determines a rising point of the curve $C_4$, and determines, as a systolic BP value $BP_{SYS}$, a cuff pressure $PK_1$ corresponding to the rising point. The rising point of the curve $C_4$ may be determined by determining a regression line of a predetermined number of successive amplitude differences $\Delta A$ and specifying a point where the rate of change of the slope of the regression line first exceeds a predetermined value. Alternatively, the rising point may be determined by specifying a point where the curve $C_4$ first exceeds a predetermined reference value equal to, e.g., 10% of the greatest one of all the amplitude differences $\Delta A$.

Next, there will be described the operation of the control device 40 of the BP measuring apparatus 10 constructed as described above, by reference to the flow chart of FIG. 5.

The control device 40 begins with the control routine represented by the flow chart of FIG. 5, in response to operation of a measurement-start switch (not shown).

First, the control device 40 carries out Steps S1, S2, and S3 of FIG. 5 corresponding to the cuff-pressure changing means 60. At Step S1, the control device 40 starts the air pump 28, and switches the switch valve 22 to its pressure-supply state, to start increasing the pressure of the cuff 12, i.e., the respective pressures of the first and second rubber bags 18, 14.

At the following step; Step S2, the control device 40 judges whether the cuff pressure $PK_1$ has reached the predetermined target pressure $P_{CM}$ (e.g., 230 mmHg) as the pressing pressure which can completely stop the flow of blood in the arteries 21 under the cuff 12. If a negative judgment is made at Step S2, Steps S1 and S2 are repeated to continue increasing the pressing pressure of the cuff 12, i.e., the cuff pressure $PK_1$.

On the other hand, if a positive judgment is made at Step S2, the control of the control device 40 goes to Step S3 to switch the switch valve 22 to its slow-deflation state to slowly decrease the pressing pressure of the cuff 12 at the predetermined low rate of 3 mmHg/sec. That is, the first pressure $P_1$ in the first rubber bag 18 and the second pressure $P_2$ in the second rubber bag 14 start slowly decreasing.

At the following step, Step S4, the control device 40 reads in the cuff-pressure signal $SK_1$ supplied from the static-pressure filter circuit 34, the first pulse-wave signal $SM_1$ supplied from the first pulse-wave filter circuit 36, and the second pulse-wave signal $SM_2$ supplied from the second pulse-wave filter circuit 44.

Subsequently, the control goes to Steps S5 and S6 corresponding to the cuff-pressure changing means 60. At Step S5, the control device 40 judges whether the cuff pressure $PK_1$ has reached the measurement-end pressure value $P_{CE}$ which is predetermined as a value sufficiently lower than the diastolic BP value $BP_{DIA}$ of the subject. If a negative judgment is made at Step S5, Steps S4 and S5 are repeated to continue decreasing the cuff pressure $PK_1$ and reading the three signals $SK_1$, $SM_1$, $SM_2$. On the other hand, if a positive judgment is made at Step S5, the control of the control device 40 goes to Step S6 to switch the switch valve 22 to its quick-deflation state to quickly decrease the pressure of the cuff 12 down to zero.

At the following step, Step S7, corresponding to the first-amplitude determining means 62, the control device 40 determines a first amplitude $A_1$ of each of the successive heartbeat-synchronous pulses of the first pulse-wave signal $SM_1$ read at Step S4, and stores the determined first amplitude $A_1$ of the each pulse, together with a cuff pressure $PK_1$ detected when the each pulse is detected, in the first-amplitude memory area of the RAM 50. That is, a group of first amplitudes $A_1$ and a group of corresponding cuff pressure values $PK_1$ are stored in the first-amplitude memory area of the RAM 50.

At the following step, Step S8, corresponding to the second-amplitude determining means 64, the control device 40 determines a second amplitude $A_2$ of each of the successive heartbeat-synchronous pulses of the second pulse-wave signal $SM_2$ read at Step S4, and stores the determined second amplitude $A_2$ of the each pulse, together with a cuff pressure $PK_1$ detected when the each pulse is detected, in the second-amplitude memory area of the RAM 50. That is, a group of second amplitudes $A_1$ and a group of corresponding cuff pressure values $PK_1$ are stored in the second-amplitude memory area of the RAM 50.

At the following step, Step S9, corresponding to the amplification-factor determining means 66, the control device 40 determines, based on the first and second amplitudes $A_1$, $A_2$ that are determined at Steps S7, S8 and correspond to the heartbeat-synchronous pulses of the first and second pulse-wave signals $SM_1$, $SM_2$ detected in the blood-stop pressure range of the cuff pressure $PK_1$ between the target pressure $P_{CM}$ and the predetermined reference pressure $P_B$ (e.g., 210 mmHg), an amplification factor N to be used to amplify the second amplitudes $A_2$ so that the amplified second amplitudes $A_2$ corresponding to the pulses of the second signal $SM_2$ detected in the blood-stop pressure range are substantially equal to the first amplitudes $A_1$ corresponding to the pulses of the first signal $SM_1$ detected in the blood-stop pressure range. For example, the means 66 determines, as the factor N, a value obtained by dividing an average of the first amplitudes $A_1$ corresponding to the pulses of the first signal $SM_1$ detected in the blood-stop pressure range, by an average of the second amplitudes $A_2$ corresponding to the pulses of the second signal $SM_1$ detected in the blood-stop pressure range.

At the following step, Step S10, corresponding to the amplitude correcting means 68, the control device 40 corrects the second amplitudes $A_2$ determined at Step S8, by calculating the product of each of the second amplitudes $A_2$ and the amplification factor N determined at Step S9, so that the amplified second amplitudes $A_2$ corresponding to the pulses of the second signal $SM_2$ detected in the blood-stop pressure range are substantially equal to the first amplitudes $A_1$ corresponding to the pulses of the first signal $SM_1$ detected in the blood-stop pressure range. Thus, the control device 40 provides the corrected amplitudes $A_{2-1}$ shown as the curve $C_3$ in FIG. 4.

At the following step, Step S11, corresponding to the amplitude-difference determining means 70, the control device 40 calculates a difference $\Delta A$ of each of the corrected amplitudes $A_{2-1}$ obtained at Step S10 and a corresponding one of the first amplitudes $A_1$ obtained at Step S7, by subtracting, from the each corrected amplitude $A_{2-1}$, the corresponding first amplitude $A_1$. Thus, the control device 40 provides the amplitude differences $\Delta A$ shown as the curve $C_4$ in FIG. 4.

At the following step, Step S12, corresponding to the BP determining means 72, the control device 40 determines, according to the conventional oscillometric method, one or more BP values (e.g., a systolic BP value $BP_{SYS}$, a mean BP value $BP_{MEAN}$, and/or a diastolic BP value $BP_{DIA}$) of the subject based on the amplitude differences $\Delta A$ determined at Step S11. For example, the control device 40 identifies an amplitude difference $\Delta A$ which first exceeds, as the cuff pressure $PK_1$ decreases, a reference value equal to 10% of the greatest one of all the amplitude differences $\Delta A$, and determines, as a systolic BP value $BP_{SYS}$, a cuff pressure $PK_1$ detected when the pulse corresponding to the thus identified amplitude difference $\Delta A$ is detected. The control device 40 determines, as a mean BP value $BP_{MEAN}$, a cuff pressure $SK_1$ detected when the pulse corresponding to the greatest amplitude difference $\Delta A$ or the greatest first amplitude $A_1$ is detected, and determines a diastolic BP value $BP_{DIA}$, based on the change of the amplitude differences $\Delta A$ or the change of the first amplitudes $A_1$ according to the oscillometric method.

At the following step, Step S13, the control device 40 operates the display device 52 to display the BP value or values BP determined at Step S12. Thus, one control cycle according to the control routine of FIG. 5 ends.

It emerges from the foregoing description that in the illustrated embodiment the amplitude correcting means 68 (Step S10) corrects all the second amplitudes $A_2$ detected by the second pulse-wave detecting device 45, so that the corrected second amplitudes $A_2$ corresponding to the pulses of the second pulse-wave signal $SM_2$ detected from the second rubber bag 14 in the blood-stop pressure range are substantially equal to the first-amplitudes $A_1$ corresponding to the pulses of the first pulse-wave signal $SM_1$ detected from the first rubber bag 18 in the blood-stop pressure range, and that the amplitude-difference determining means 70 (Step S11) determines a difference $\Delta A$ between each of the second amplitudes $A_{2-1}$ corrected by the means 68 and a corresponding one of the first amplitudes $A_1$ detected from the first rubber bag 18. The thus obtained amplitude differences $\Delta A$ (i.e., the curve $C_4$ shown in FIG. 4) have a clear rising point. The BP determining means 72 (Step S12) determines one or more BP values BP of the subject based on the change of the amplitude differences $\Delta A$ (or the curve $C_4$) determined by the means 70. Therefore, the present BP measuring apparatus 10 can measure one or more accurate BP values BP of the subject.

In addition, the second pulse-wave detecting device 45 includes the second rubber bag 14 which is supported by the cuff 12 such that the second bag 14 is located inside the downstream-side portion of the first ribber bag 18 as seen in the direction in which the blood flows in the arteries 21, and which has a width as measured in that direction that is smaller than the width of the first bag 18 in the same direction, and the second pressure sensor 32 which detects the pulse wave produced from the arteries 21 and propagated to the second bag 14, and which produces the second pulse-wave signal $SM_2$ representing the detected pulse wave. Since the present BP measuring apparatus 10 enjoys a simple construction owing to this arrangement of the second pulse-wave detecting device 45, the apparatus 10 can be produced with ease and at low cost.

While the present invention has been described in its preferred embodiment, the present invention may be otherwise embodied.

For example, in the illustrated embodiment, the amplitude correcting means 68 corrects the second amplitudes $A_2$ so that a certain portion of the corrected second amplitudes $A_{2-1}$ are substantially equal to a corresponding portion of the first amplitudes $A_1$. However, the amplitude correcting means 68 may correct, for the same purpose, the first amplitudes $A_2$, or both the first and second amplitudes $A_1$, $A_2$.

In the illustrated embodiment, the cuff 12 employed is for being worn on an ankle 19 of a living subject. However, the cuff 12 may be one which is for being wound around any other body portion of the subject than the ankle 19, such as a femur or an upper arm.

In the illustrated embodiment, the second rubber bag 14 has substantially the same length as that of the first rubber bag 18, in the circumferential direction of the ankle 19 of the subject. However, the second bag 14 is employed for detecting the pulse wave produced from the arteries 21 of the ankle 19 around which the cuff 12 is wound. Therefore, the second bag 14 is required to have a length which assures that the bag 14 can be located right above at least one artery 21. Thus, the second bag 14 may be shorter than the first bag 18.

In the illustrated embodiment, the BP determining means 72 (Step S12) processes signals and thereby determines BP values BP after the slow decreasing of the pressing pressure of the cuff 12 has been completed. However, the means 72 may process the signals and determine the BP values while the pressing pressure of the cuff 12 is slowly decreased by the cuff-pressure changing means 60.

Alternatively, the BP determining means 72 may process signals and thereby determine BP values BP after, or while, the pressure of the cuff 12 is slowly increased by the cuff-pressure changing means 60.

In the illustrated embodiment, the diameter of the pipe 30 is smaller than that of the pipe 20, so that the pipe 30 functions as a restrictor. However, the pipe 30 may be one which has the same diameter as that of the pipe 20, in the case where an orifice is provided in the pipe 30.

In the illustrated embodiment, the single air pump 28 and the single switch valve 22 can be used for changing both the first pressure $P_1$ in the first rubber bag 18 and the second pressure $P_2$ in the second rubber bag 14, because the small-diameter pipe 30 functions as the restrictor. However, exclusive air pumps and exclusive switch valves may be employed for the first and second rubber bags 18, 14, respectively.

In the illustrated embodiment, the second rubber bag 14 is located inside the most downstream-side portion (e.g., downstream-side end portion) of the first rubber bag 18. However, the second bag 14 may be provided inside any portion of the downstream-side half portion of the first bag 18.

In the illustrated embodiment, the second pulse-wave detecting device 45 includes the second rubber bag 14 provided inside the downstream-side portion of the first rubber bag 18, and the pressure sensor 32 for detecting the pulse wave propagated to the second bag 14. However, the second pulse-wave detecting device 45 may be a different one. For example, the device 45 may be one which includes a reflecting plate which is provided inside a substantially central portion of the first rubber bag 18, and an optical distance sensor which is provided inside the cuff, at a position opposite to the reflecting plate with respect to an artery located therebetween, and which includes a light emitter and a light receiver. In the last case, when the artery under the cuff pulsates, the distance between the optical distance sensor and the reflecting plate changes, and this change is detected as a pulse wave. Therefore, the pulse wave detected by this pulse-wave detecting device is influenced by a pulse wave propagated to the first rubber bag 18.

In the illustrated embodiment, the second amplitudes $A_2$ are multiplied by the amplification factor N, and thereby corrected into the corrected amplitudes $A_{2-1}$, and the first amplitudes $A_1$ are subtracted from the corrected amplitudes $A_{2-1}$, to obtain the amplitude differences $\Delta A$. That is, the electronic control device 40 obtains, by calculation, the amplitude differences $\Delta A$. However, a pressure-difference sensor whose one end is connected to the pipe 30 and whose other end is connected to the pipe 20 may be employed to determine amplitude differences $\Delta A$. In this case, the pressure-difference sensor may employ a sensitivity amplifying device which detects the pressure in the pipe 30 with a sensitivity "M" times higher than a sensitivity with which the device detects the pressure in the pipe 20. This number M corresponds to the amplification factor N. The sensitivity amplifying device may be a pressure decreasing device which is provided on a pressure-receiving surface to receive the pressure in the pipe 20 and which decreases, to 1/M, the pressure to be received by the pressure-receiving surface. Alternatively, the sensitivity amplifying device may be provided by constructing the pressure-difference sensor such that a pressure-receiving surface to receive the pressure in the pipe 30 has an area M times greater than that of the pressure-receiving surface to receive the pressure in the pipe 20.

It is to be understood that the present invention may be embodied with other changes, improvements, and modifications that may occur to a person skilled in the art without departing from the scope and spirit of the invention defined in the appended claims.

What is claimed is:

1. A blood-pressure measuring apparatus, comprising:
    an inflatable cuff which is adapted to be wound around a body portion of a living subject and which includes a first inflatable bag which is inflatable to press an arterial vessel of the body portion and stop flow of blood in the arterial vessel;
    a first pulse-wave detecting device which detects a first pulse wave which is produced from the arterial vessel and is propagated to the first inflatable bag of the cuff wound around the body portion, the first pulse wave including a plurality of heartbeat-synchronous pulses;
    a second pulse-wave detecting device which detects a second pulse wave which is produced from the arterial vessel and is propagated to a downstream-side portion of the cuff wound around the body portion as seen in a direction in which the blood flows in the arterial vessel, the second pulse wave including a plurality of heartbeat-synchronous pulses;
    amplitude correcting means for correcting at least one of (a) a first group of respective amplitudes of the heartbeat-synchronous pulses of the first pulse wave detected by the first pulse-wave detecting device and (b) a second group of respective amplitudes of the heartbeat-synchronous pulses of the second pulse wave detected by the second pulse-wave detecting device, so that at least one amplitude of the first group that corresponds to at least one heartbeat-synchronous pulse of the first pulse wave that is detected by the first pulse-wave detecting device while the flow of the blood in the arterial vessel is stopped by the first inflatable bag is substantially equal to at least one amplitude of the second group that corresponds to at least one heartbeat-synchronous pulse of the second pulse wave that is detected by the second pulse-wave detecting device while the flow of the blood in the arterial vessel is stopped by the first inflatable bag;
    amplitude-difference determining means for determining a difference between each of the amplitudes of the first group and a corresponding one of the amplitudes of the second group after said at least one of the first and second groups is corrected by the amplitude correcting means; and
    blood-pressure determining means for determining a blood pressure of the subject based on the difference between said each of the amplitudes of the first group and said corresponding one of the amplitudes of the second group.

2. An apparatus according to claim 1, wherein the second pulse-wave detecting device comprises:
    a second inflatable bag which is supported by the inflatable cuff such that the second inflatable bag is located inside a downstream-side portion of the first inflatable bag as seen in the direction in which the blood flows in the arterial vessel, and which has a dimension as measured in said direction that is smaller than a dimension of the first inflatable bag as measured in said direction; and
    a pressure sensor which detects the second pulse wave produced from the arterial vessel and propagated to the second inflatable bag, and which produces an electric signal representing the detected second pulse wave including the heartbeat-synchronous pulses having the respective amplitudes.

3. An apparatus according to claim 2, further comprising a preventing member which prevents the first pulse wave from being transmitted from the first inflatable bag to the second inflatable bag.

4. An apparatus according to claim 2, wherein the first pulse-wave detecting device comprises a pressure sensor which detects the first pulse wave produced from the arterial vessel and propagated to the first inflatable bag, and which produces an electric signal representing the detected first pulse wave including the heartbeat-synchronous pulses having the respective amplitudes.

5. An apparatus according to claim 4, wherein the blood-pressure determining means comprises means for determining, as a systolic blood pressure of the subject, a pressure in the first inflatable bag that is detected by the pressure sensor of the first pulse-wave detecting device, at a time when the respective differences between the amplitudes of the first group and the corresponding amplitudes of the second group significantly change as the pressure of the first inflatable bag changes.

6. An apparatus according to claim 1, further comprising a pressure changing device which changes a pressure in the first inflatable bag of the cuff wound around the body portion to press the arterial vessel and stop the flow of the blood in the arterial vessel.

7. An apparatus according to claim 1, further comprising:
   first amplitude determining means for determining the respective amplitudes of the heartbeat-synchronous pulses of the first pulse wave that are detected by the first pulse-wave detecting device while the pressure of the first inflatable bag is changed by the pressure changing device, and thereby providing the first group of amplitudes; and
   second amplitude determining means for determining the respective amplitudes of the heartbeat-synchronous pulses of the second pulse wave that are detected by the second pulse-wave detecting device while the pressure of the first inflatable bag is changed by the pressure changing device, and thereby providing the second group of amplitudes.

8. An apparatus according to claim 1, wherein the amplitude correcting means comprises:
   amplification-factor determining means for determining an amplification factor based on at least one amplitude of the first group that corresponds to said at least one heartbeat-synchronous pulse of the first pulse wave that is detected by the first pulse-wave detecting device while the flow of the blood in the arterial vessel is stopped by the first inflatable bag, and at least one amplitude of the second group that corresponds to said at least one heartbeat-synchronous pulse of the second pulse wave that is detected by the second pulse-wave detecting device while the flow of the blood in the arterial vessel is stopped by the first inflatable bag; and
   calculating means for calculating a product of the amplification factor and each of the amplitudes of said at least one of the first and second groups, and thereby correcting said at least one of the first and second groups.

9. An apparatus according to claim 1, wherein the amplification-factor determining means comprises means for determining the amplification factor by dividing an average of a plurality of amplitudes of the first group that corresponds to a plurality of heartbeat-synchronous pulse of the first pulse wave that are detected by the first pulse-wave detecting device while the flow of the blood in the arterial vessel is stopped by the first inflatable bag, by an average of a plurality of amplitudes of the second group that corresponds to a plurality of heartbeat-synchronous pulse of the second pulse wave that are detected by the second pulse-wave detecting device while the flow of the blood in the arterial vessel is stopped by the first inflatable bag, and wherein the calculating means calculates a product of the amplification factor and each of the amplitudes of the second groups, and thereby correcting the second groups, and the amplitude-difference determining means determines a difference between each of the amplitudes of the first group and a corresponding one of the amplitudes of the second group that have been corrected by the amplitude correcting means.

10. An apparatus according to claim 1, further comprising a display device which displays the blood pressure of the subject determined by the blood-pressure determining means.

* * * * *